United States Patent
Hakala et al.

(10) Patent No.: US 10,517,621 B1
(45) Date of Patent: Dec. 31, 2019

(54) METHOD OF MANAGING ENERGY DELIVERED BY A SHOCKWAVE THROUGH DWELL TIME COMPENSATION

(71) Applicant: Shockwave Medical, Inc., Santa Clara, CA (US)

(72) Inventors: Doug Hakala, Woodinville, WA (US); John M. Adams, Snohomish, WA (US); Randy Holmberg, Bothell, WA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 16/554,497

(22) Filed: Aug. 28, 2019

Related U.S. Application Data

(63) Continuation-in-part of application No. 16/222,679, filed on Dec. 17, 2018, which is a continuation of
(Continued)

(51) Int. Cl.
*A61B 17/22* (2006.01)
*A61B 17/225* (2006.01)
*A61B 17/00* (2006.01)

(52) U.S. Cl.
CPC ...... *A61B 17/22022* (2013.01); *A61B 17/225* (2013.01); *A61B 2017/00039* (2013.01);
(Continued)

(58) Field of Classification Search
CPC ............ A61B 17/225; A61B 17/22022; A61B 2017/00039; A61B 2017/22025; A61B 2017/22065
See application file for complete search history.

(56) References Cited

U.S. PATENT DOCUMENTS 3,413,976 A  12/1968 Roze
3,785,382 A  1/1974  Schmidt-Kloiber et al.
(Continued)

FOREIGN PATENT DOCUMENTS

CN  1204242 A  1/1999
CN  1269708 A  10/2000
(Continued)

OTHER PUBLICATIONS

Ardley, Tim, "First Principles of a Gas Discharge Tube (GDT) Primary Protector", Bourns, Rev. 2, Available Online at <https://www.mouser.com/pdfdocs/bourns_gdt_white_paper.pdf>, 2008, pp. 1-34.
(Continued)

*Primary Examiner* — Tuan V Nguyen
(74) *Attorney, Agent, or Firm* — Morrison & Foerster LLP

(57) ABSTRACT

A method of delivering shock waves to treat calcified lesions includes advancing an angioplasty balloon mounted on a carrier, to reach the calcified lesion. A pair of electrodes is located within the balloon. The balloon is filled with a conductive fluid. A series of high voltage pulses are supplied to the electrodes. Each voltage pulse has sufficient energy to generate an arc in the fluid and allows current to flow across the pair of electrodes to produce a shock wave. During each pulse, the current flowing across the pair of electrodes is monitored. When the sensed current reaches a predetermined value, that voltage pulse is terminated. The predetermined value is selected to be high enough to ensure the creation of the arc while compensating for the variable dwell time between initial application of a given voltage pulse and creation of the arc.

20 Claims, 5 Drawing Sheets

Related U.S. Application Data application No. 15/065,607, filed on Mar. 9, 2016, now Pat. No. 10,159,505, which is a continuation of application No. 13/615,107, filed on Sep. 13, 2012, now Pat. No. 9,333,000.

(52) U.S. Cl.
CPC .............. *A61B 2017/22025* (2013.01); *A61B 2017/22065* (2013.01)

(56) References Cited

U.S. PATENT DOCUMENTS

| | | |
|---|---|---|
| 3,902,499 A | 9/1975 | Shene |
| 4,027,674 A | 6/1977 | Tessler et al. |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,900,303 A | 2/1990 | Lemelson |
| 5,009,232 A | 4/1991 | Hassler et al. |
| 5,057,103 A | 10/1991 | Davis |
| 5,057,106 A | 10/1991 | Kasevich et al. |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,176,675 A | 1/1993 | Watson et al. |
| 5,245,988 A | 9/1993 | Einars et al. |
| 5,246,447 A | 9/1993 | Rosen et al. |
| 5,281,231 A | 1/1994 | Rosen et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | de la Torre et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,083,232 A | 7/2000 | Cox |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,241,295 B2 | 7/2007 | Maguire |
| 7,505,812 B1 | 3/2009 | Eggers et al. |
| 7,569,032 B2 | 8/2009 | Naimark et al. |
| 8,556,813 B2 | 10/2013 | Cioanta et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 9,005,216 B2 | 4/2015 | Hakala et al. |
| 9,011,463 B2 | 4/2015 | Adams et al. |
| 9,333,000 B2 | 5/2016 | Hakala et al. |
| 9,522,012 B2 | 12/2016 | Adams |
| 10,159,505 B2 | 12/2018 | Hakala et al. |
| 2001/0044596 A1 | 11/2001 | Jaafar |
| 2002/0045890 A1 | 4/2002 | Celliers et al. |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0113722 A1 | 5/2005 | Schultheiss |
| 2005/0113822 A1 | 5/2005 | Fuimaono et al. |
| 2005/0228372 A1 | 10/2005 | Truckai et al. |
| 2005/0251131 A1 | 11/2005 | Lesh |
| 2006/0004286 A1 | 1/2006 | Chang et al. |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0282301 A1 | 12/2007 | Segalescu et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0203255 A1 | 8/2012 | Hawkins et al. |
| 2012/0221013 A1 | 8/2012 | Hawkins et al. |
| 2013/0030431 A1 | 1/2013 | Adams |
| 2013/0030447 A1 | 1/2013 | Adams |
| 2013/0041355 A1 | 2/2013 | Heeren et al. |
| 2013/0150874 A1 | 6/2013 | Kassab |
| 2014/0005576 A1 | 1/2014 | Adams et al. |
| 2014/0039513 A1 | 2/2014 | Hakala et al. |
| 2014/0046229 A1 | 2/2014 | Hawkins et al. |
| 2014/0052145 A1 | 2/2014 | Adams et al. |
| 2014/0052147 A1 | 2/2014 | Hakala et al. |
| 2014/0243820 A1 | 8/2014 | Adams et al. |
| 2015/0073430 A1 | 3/2015 | Hakala et al. |
| 2015/0238208 A1 | 8/2015 | Adams et al. |

(56) References Cited

U.S. PATENT DOCUMENTS

| | | |
|---|---|---|
| 2017/0056035 A1 | 3/2017 | Adams |
| 2019/0254692 A1 | 8/2019 | Hakala et al. |

FOREIGN PATENT DOCUMENTS

| | | |
|---|---|---|
| CN | 1942145 A | 4/2007 |
| CN | 102057422 A | 5/2011 |
| CN | 102271748 A | 12/2011 |
| CN | 102765785 A | 11/2012 |
| DE | 3038445 A1 | 5/1982 |
| EP | 0442199 A2 | 8/1991 |
| EP | 0571306 A1 | 11/1993 |
| JP | 62-275446 A | 11/1987 |
| JP | 6-125915 A | 5/1994 |
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| JP | 2007-289707 A | 11/2007 |
| JP | 2007-532182 A | 11/2007 |
| JP | 2008-506447 A | 3/2008 |
| JP | 2011-524203 A | 9/2011 |
| JP | 2012-508042 A | 4/2012 |
| WO | 1996/024297 A1 | 8/1996 |
| WO | 1999/02096 A1 | 1/1999 |
| WO | 2004/069072 A2 | 8/2004 |
| WO | 2005/099594 A1 | 10/2005 |
| WO | 2005/102199 A1 | 11/2005 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 2010/014515 A2 | 2/2010 |
| WO | 2011/143468 A2 | 11/2011 |
| WO | 2013/059735 A1 | 4/2013 |

OTHER PUBLICATIONS

Bank of America Merrill Lynch, "A Simple Solution to a Difficult (and Large) Problem—Initiating Coverage of SWAV", Shockwave Medical Inc., Apr. 1, 2019, pp. 1-22.

Bittl et al., "Coronary Artery Perforation during Excimer Laser Coronary Angioplasty", Journal of the American College of Cardiology, vol. 21, No. 5, Apr. 1993, pp. 1158-1165.

Bittl et al., "Publication Information—Coronary Artery Perforation during Excimer Laser Coronary Angioplasty", Journal of the American College of Cardiology, vol. 21, No. 5, Apr. 1993, pp. 1-6.

Brinton et al., "Publication Information—TCT-777 Safety and Performance of the Shockwave Medical Lithoplasty® System in Treating Calcified Peripheral Vascular Lesions: 6-Month Results from the Two-Phase DISRUPT PAD Study", Journal of the American College of Cardiology, vol. 68, No. 18, Supplement, Nov. 2016, pp. 1-5.

Brinton et al., "TCT-777 Safety and Performance of the Shockwave Medical Lithoplasty® System in Treating Calcified Peripheral Vascular Lesions: 6-Month Results from the Two-Phase Disrupt PAD STUDY", Journal of the American College of Cardiology, vol. 68, No. 18, Supplement B, 2016, p. B314.

Broyer et al., "High-Efficiency Shock-Wave Generator for Extracorporeal Lithotripsy", Medical and Biological Engineering and Computing, vol. 34, Sep. 1996, pp. 321-328.

Cardiology Today's Intervention, "Shockwave Attracts Additional Investment from Abiomed, has IPO", Available Online at <https://www.healio.com/cardiac-vascular-intervention/peripheral/news/online/%7Bf96c1e20-b4a9-4167-bdb8-254e86a8182a%7D/shockwave-attracts-additional-investment-from-abiomed-has-ipo>, Mar. 12, 2019, pp. 1-2.

Citel Inc., "Gas Discharge Overview", Available Online at <http://www.citel.us/gas_discharge_tubes_overview.html>, pp. 1-2.

Cleveland et al., "Design and Characterization of a Research Electrohydraulic Lithotripter Patterned after the Dornier HM3", Review of Scientific Instruments, vol. 71, No. 6, Jun. 2000, pp. 2514-2525.

Deagon, Brian, "Technology—Shockwave Medical IPO Soars on First Day of Trading", Investor's Business Daily, Available Online at <https://www.investors.com/news/technology/shockwave-medical-ipo-soars-trading/>, Mar. 7, 2019, pp. 1-15.

Decision of Inter Partes Review for U.S. Pat. No. 8,728,091, by the Patent Trial and Appeal Board dated Jul. 11, 2019, pp. 1-32.

Declaration of Dr. Morten Olgaard Jensen, Dec. 6, 2018, 138 pages.

Declaration of Natalie J. Grace on Apr. 14, 2019, pp. 1-5.

Declaration of William Patrick Stephens on Apr. 14, 2019, pp. 1-6.

Dodd, A. T. S., "Two Cases of Calculus in the Bladder, in which Lithotripsy was Performed", Provincial Medical & Surgical Journal, vol. 3, No. 71, 1842, pp. 368-370.

Elmansy et al., "Publication Information—Recent Advances in Lithotripsy Technology and Treatment Strategies: A Systematic Review Update", International Journal of Surgery, vol. 36, Part D, Dec. 2016, pp. 1-6.

Elmansy et al., "Recent Advances in Lithotripsy Technology and Treatment Strategies: A Systematic Review Update", International Journal of Surgery, vol. 36, 2016, pp. 676-680.

"FDA Clears Lithoplasty Balloon That Shatters Calcified Lesions With Ultrasound", Diagnostic and Interventional Cardiology, Available Online at <https://www.dicardiology.com/product/fda-clearslithoplasty-balloon-shatters-calcified-lesions-ultrasound>, Sep. 16, 2016, pp. 1-5.

Grocela et al., "Intracorporeal Lithotripsy. Instrumentation and Development", Urologic Clinics of North America, vol. 24, No. 1, Feb. 1997, pp. 13-23.

Kaplan et al., "Healing after Arterial Dilatation with Radiofrequency Thermal and Nonthermal Balloon Angioplasty Systems", Journal of Investigative Surgery, vol. 6, 1993, pp. 33-52.

Knight, D. W., "Gas Discharge Tubes—Introduction", G3YNH. info, Available Online at <http://g3ynh.info/disch_tube/intro.html>, 2013, pp. 1-9.

Manousakas et al., "A High-Voltage Discharging System for Extracorporeal Shock-Wave Therapy", IFMBE Proceedings, vol. 23, 2009, pp. 706-707.

Mills et al., "Cracking the Code on Calcium; Initiate with BUY, $39 Target", Canaccord Genuity—Capital Markets, US Equity Research, Apr. 1, 2019, pp. 1-63.

Mitomo, Satoru, "Intravascular lithotripsy: A Novel Technology for Treating Calcified Coronary Stenoses", Cardiovascular News, Online Available at <https://cardiovascularnews.com/intravascular-lithotripsy-anovel-technology-for-treating-calcified-coronary-stenoses>, Apr. 18, 2018, pp. 1-4.

Motisan, "Relaxation Oscillator Using a Hydrogen Thyratron", PocketMagic, Available Online at <https://www.pocketmagic.net/relaxation-oscillator-using-a-hydrogenthyratron)>, Oct. 9, 2011, pp. 1-5.

Nisonson et al., "Ambulatory Extracorporeal Shockwave Lithotripsy", Urology, vol. 28, No. 5, Nov. 1986, pp. 381-384.

Non-Final Office Action received for U.S. Appl. No. 15/347,486, dated Nov. 2, 2018, 8 pages.

Notice of Allowance received for U.S. Appl. No. 15/347,486, dated Aug. 29, 2019, 7 pages.

Notice of Allowance received for U.S. Appl. No. 15/347,486, dated May 23, 2019, 8 pages.

Notice of Allowance received for Chinese Patent Application No. 201380047277.3, dated Nov. 6, 2017, 2 pages (Official Copy Only) (See Communication under 37 CFR § 1.98(a) (3)).

Notice of Allowance received for Japanese Patent Application No. 2015-532052, dated Jun. 25, 2018, 3 pages (Official Copy Only) (See Communication under 37 CFR § 1.98(a) (3)).

Office Action received for Japanese Patent Application no. 2015-532052, dated Feb. 6, 2018, 9 pages (6 pages of English Translation and 3 pages of Official Copy).

Patent Owner Preliminary Response for U.S. Pat. No. 8,728,091, by the Patent Trial and Appeal Board dated Apr. 14, 2019, pp. 1-68.

(56) References Cited

OTHER PUBLICATIONS

Patterson et al., "The Etiology and Treatment of delayed Bleeding following Percutaneous Lithotripsy", The Journal of Urology, vol. 133, 1985, pp. 447-451.
Petition for Inter Partes Review of U.S. Pat. No. 8,728,091, issued on May 20, 2014, 74 pages.
Prosecution History of U.S. Appl. No. 14/079,463, issued as U.S. Pat. No. 8,728,091, 860 pages.
Ricks, Delthia, "Long Island Doctors Using Sound Waves to Loosen Calcium Deposits from Arteries, Restore Blood Flow", News/Health, Available Online at <https://www.newsday.com/news/health/calcium-treatment-st-francis-hospital-1.27314331>, Feb. 15, 2019, pp. 1-4.
Shockwavemedical.com, "Intravascular Lithotripsy (IVL)", Available Online at <https://shockwavemedical.com/technology/intravascular-lithotripsy-ivl/?country=Egypt>, 2019, pp. 1-4.
Tanaka et al., "A New Radiofrequency Thermal Balloon Catheter for Pulmonary Vein Isolation", Journal of the American College of Cardiology, vol. 38, No. 7, Dec. 2001, pp. 2079-2086.
Texas Instruments, "Power Management Guide", Available Online at <http://www.ti.com/lit/sg/slvt145r/slvt145r.pdf>, 2018, pp. 1-93.
"Top Cardiovascular Innovation Award", Cardiovascular Research Technologies (CRT), 2015, p. 1.
U.S. 2003/0176873, Chernenko et al., "Chernenko Drawings", Fig. 4b and Fig. 5 from Drawings as filed on Mar. 12, 2002, pp. 1-2.
Wells Fargo Securities LLC, "SWAV: Initiating With a Market Perform Rating", Shockwave Medical Inc., Apr. 1, 2019, pp. 1-34.
Zhong et al., "Publication Information—Transient Oscillation of Cavitation Bubbles Near Stone Surface During Electrohydraulic Lithotripsy", Journal of Endourology, vol. 11, No. 1, 1997, 1 page.
Advisory Action received for U.S. Appl. No. 13/615,107, dated Nov. 6, 2015, 3 pages.
Advisory Action received for U.S. Appl. No. 12/482,995, dated Jun. 2, 2014, 3 pages.
Advisory Action received for U.S. Appl. No. 12/482,995, dated Sep. 29, 2011, 2 pages.
Advisory Action received for U.S. Appl. No. 12/581,295, dated Jul. 3, 2014, 3 pages.
Advisory Action received for U.S. Appl. No. 13/049,199, dated Jun. 7, 2012, 3 pages.
Advisory Action received for U.S. Appl. No. 13/267,383, dated Jan. 6, 2014, 4 pages.
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol., vol. 95, 2003, pp. 67-75.
Decision to Grant received for European Patent Application No. 13756766.5, dated May 27, 2016, 2 pages.
Decision to Grant received for Japanese Patent Application No. 2011-513694, dated Oct. 7, 2014, 3 pages.
Extended European Search Report (includes Supplementary European Search Report and Search Opinion) received for European Patent Application No. 09763640.1, dated Oct. 10, 2013, 5 pages.
Extended European Search Report received for European Patent Application No. 13827971.6, dated Apr. 12, 2016, 8 pages.
Final Office Action received for U.S. Appl. No. 12/482,995, dated Jul. 22, 2011, 14 pages.
Final Office Action received for U.S. Appl. No. 12/501,619, dated Feb. 21, 2012, 12 pages.
Final Office Action received for U.S. Appl. No. 12/581,295, dated Mar. 28, 2013, 8 pages.
Final Office Action received for U.S. Appl. No. 13/049,199, dated Apr. 4, 2012, 10 pages.
Final Office Action received for U.S. Appl. No. 14/271,342, dated Feb. 27, 2015, 7 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 13/049,199, dated Aug. 11, 2014, 8 pages.
Final Office Action received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107, dated Sep. 1, 2015, 9 pages.
Final Office Action received for U.S. Appl. No. 13/646,570, dated Dec. 23, 2014, 10 pages.
Gambihler et al., "Permeabilization of the Plasma Membrane of LI210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep vol. 14, 2012, pp. 567-572.
Intention to Grant received for European Patent Application No. 13756766.5, dated Jan. 8, 2016, 5 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987, dated Nov. 20, 2014, 11 pages.
International Preliminary Report on Patentability received for PCT Patent Application No. PCT/US2013/048277, dated Jan. 8, 2015, 9 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533, dated Mar. 26, 2015, 10 pages.
International Search Report and Written Opinion received for PCT Patent Application No. PCT/US2013/031805, dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report received for PCT Patent Application No. PCT/US2009/047070, dated Jan. 19, 2010, 4 pages.
International Search Report received for PCT Patent Application No. PCT/US2012/023172, dated Sep. 28, 2012, 3 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
International Written Opinion received for PCT Patent Application No. PCT/US2009/047070, dated Jan. 19, 2010, 5 pages.

(56) References Cited

OTHER PUBLICATIONS

Kodama et al., "Shock wave-mediated molecular delivery into cells", Biochimica et Biophysica Acta, vol. 1542, 2002, pp. 186-194.
Lauer et al., "Shock Wave Permeabilization as a New Gene Transfer Method", Gene Therapy vol. 4, 1997, pp. 710-715.
Non-Final Office Action received for U.S. Appl. No. 12/482,995, dated Aug. 13, 2014, 10 pages.
Non-Final Office Action received for U.S. Appl. No. 12/482,995, dated Jul. 12, 2013, 11 pages.
Non-Final Office Action received for U.S. Appl. No. 13/465,264, dated Oct. 29, 2014, 13 pages.
Non-Final Office Action received for U.S. Appl. No. 13/646,570, dated Oct. 29, 2014, 10 pages.
Non-Final Office Action received for U.S. Appl. No. 14/079,463, dated Mar. 4, 2014, 9 pages.
Non-Final Office Action received for U.S. Appl. No. 12/482,995, dated Feb. 11, 2011, 27 pages.
Non-Final Office Action received for U.S. Appl. No. 12/501,619, dated Nov. 3, 2011, 10 pages.
Non-Final Office Action received for U.S. Appl. No. 12/581,295, dated Dec. 21, 2012, 9 pages.
Non-Final Office Action received for U.S. Appl. No. 12/581,295, dated Jun. 8, 2012, 9 pages.
Non-Final Office Action received for U.S. Appl. No. 13/049,199, dated Dec. 12, 2011, 10 pages.
Non-Final Office Action received for U.S. Appl. No. 13/267,383, dated Apr. 19, 2013, 6 pages.
Non-Final Office Action received for U.S. Appl. No. 13/534,658, dated Mar. 11, 2016, 12 pages.
Non-Final Office Action received for U.S. Appl. No. 14/218,858, dated Mar. 30, 2016, 13 pages.
Non-Final Office Action received for U.S. Appl. No. 14/515,130, dated Jan. 14, 2016, 16 pages.
Non-Final Office Action received for Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 13/049,199, dated Feb. 4, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 15/065,607, dated Feb. 22, 2018, 8 pages.
Notice of Acceptance Received for Australian Patent Application No. 2009257368, dated Aug. 28, 2014, 2 pages.
Notice of Acceptance received for Australian Patent Application No. 2013315444, dated Jul. 26, 2017, 3 pages.
Notice of Allowance received for Canadian Patent Application No. 2,727,429, dated May 26, 2015, 1 page.
Notice of Allowance received for U.S. Appl. No. 14/515,130, dated May 2, 2016, 8 pages.
Notice of Allowance received for U.S. Appl. No. 14/515,130, dated May 25, 2016, 3 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 13/465,264, dated May 8, 2015, 7 pages.
Notice of Allowance received for U.S. Appl. No. 14/271,276, dated Feb. 25, 2015, 8 pages.
Notice of Allowance received for U.S. Appl. No. 12/482,995, dated Dec. 24, 2014, 6 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,342, dated Mar. 13, 2015, 5 pages.
Notice of Allowance received for U.S. Appl. No. 15/065,607, dated Aug. 10, 2018, 7 pages.
Notice of Allowance received for U.S. Appl. No. 13/615,107, dated Dec. 31, 2015, 10 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Australian Patent Application No. 2013315444, dated Nov. 30, 2016, 3 pages.
Office Action received for Canadian Patent Application No. 2,727,429, dated Apr. 14, 2015, 4 pages.
Office Action received for Chinese Patent Application No. 201380033808.3, dated Jul. 5, 2016, 9 pages.
Office Action received for Chinese Patent Application No. 201380041656.1, dated Jul. 5, 2016, 9 pages.
Office Action received for Chinese Patent Application No. 201380047277.3, dated Aug. 19, 2016, 12 pages.
Office Action received for Chinese Patent Application No. 201380047277.3, dated Mar. 1, 2017, 10 pages.
Office Action received for Chinese Patent Application No. 201380047277.3, dated May 16, 2017, 13 pages.
Office Action received for Chinese Patent Application No. 201380042887.4, dated Aug. 8, 2016, 9 pages.
Office Action received for Japanese Patent Application No. 2011-513694, dated Aug. 27, 2013, 6 pages.
Office Action received for Japanese Patent Application No. 2011-513694, dated Jun. 10, 2014, 4 pages.
Office Action received for Japanese Patent Application No. 2014-158517, dated May 19, 2015, 5 pages.
Office Action received for Japanese Patent Application No. 2015-532052, dated Aug. 21, 2017, 12 pages.
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electrohydraulic Lithotripsy", Journal of Endourology, vol. 11, No. 1, Feb. 1997, pp. 55-61.

METHOD OF MANAGING ENERGY DELIVERED BY A SHOCKWAVE THROUGH DWELL TIME COMPENSATION

CROSS-REFERENCE TO RELATED APPLICATIONS

This application is a continuation-in-part of U.S. patent application Ser. No. 16/222,679, filed Dec. 17, 2018, which is a continuation of application of U.S. application Ser. No. 15/065,607, filed Mar. 9, 2016, issued as U.S. Pat. No. 10,159,505 on Dec. 25, 2018, which is a continuation of U.S. application Ser. No. 13/615,107, filed Sep. 13, 2012, issued as U.S. Pat. No. 9,333,000 on May 10, 2016 both entitled SHOCKWAVE CATHETER SYSTEM WITH ENERGY CONTROL, and each of which is hereby incorporated by reference in their entirety for all purposes.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the opening in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls.

Recently, a new system and method has been contemplated for breaking up calcium deposits in, for example, arteries and veins. Such a system is described, for example in U.S. Patent Publication No. 2009/0312768, Published Dec. 17, 2009. Embodiments described therein include a catheter having balloon, such as an angioplasty balloon, at the distal end thereof arranged to be inflated with a fluid. Disposed within the balloon is a shock wave generator that may take the form of, for example, a pair of electrodes, which are coupled to a high voltage source at the proximal end of the catheter through a connector. When the balloon is placed adjacent a calcified region of a vein or artery and a high voltage pulse is applied across the electrodes, a shock wave is formed that propagates through the fluid and impinges upon the wall of the balloon and the calcified region. Repeated pulses break up the calcium without damaging surrounding soft tissue.

Each high voltage pulse causes an arc to form across the electrodes. The arc in turn causes a steam bubble to form. Each steam bubble has the potential of producing two shock waves, a leading edge shock wave as a result of bubble expansion and a trailing edge shock wave as a result of bubble collapse. The trailing edge shock waves exhibit highly variable energy levels and generally, much greater energy levels than the leading edge shock waves. The energy levels of the trailing edge shock waves are substantially dependent on the uniformity of the bubble collapse. The uniform collapse of spherical bubbles to a point appears to create the highest shock wave energies. Unfortunately, spherical bubble configuration requires a substantially larger space than is available in a balloon that must fit into a calcified vein or artery or even a ureter. In fact, the trailing edge shock wave can be substantially eliminated by confining the bubble to an irregular shape. As a result, for angioplasty or other cardiac and non-cardiac applications of shock waves, the trailing edge shock wave cannot be reliably relied upon to produce consistent results.

However, the leading edge shock waves formed by bubble expansion are a different matter. While exhibiting generally lower energies, they are more consistent in energy level. As a result, leading edge shock waves are good candidates for use in medical procedures such, for example, angioplasty or valvuloplasty.

Another consideration is the amount of energy represented by the high voltage applied to the electrodes. Each high voltage pulse removes a portion of the electrode material. Since the size of the electrodes must be small in order to fit into the calcified vein or artery, they are only capable of sustaining a limited numbers of high voltage pulses sufficient to form the shock wave resulting electrical arc.

Also, it has been learned that to sustain a leading edge shock wave, it is not necessary to sustain the high voltage throughout the shock wave. Sustaining the high voltage beyond some point after the initial arc does not lead to shock waves of any greater intensity. Further, since the bubbles are formed of steam, the steam produces heat which can increase the temperature of adjacent soft tissue. Just a two degree Celsius elevation in temperature above body temperature can result in tissue damage.

A still further important aspect of prior art attempts to use shock waves from electrical arcs for therapeutic purposes is that from the time the high voltage is first applied to the electrodes to the time in which the arc occurs there is a dwell time (Td) that is highly variable from one high voltage application to the next. To account for the dwell times that are long, prior art strategies have relied upon high voltage applications where all high voltage pulse durations or pulse widths are of the same length and of a length sufficient to extend through the longest of the anticipated dwell times plus the associated arc and steam bubble. As a result, when the dwell times are shorter than the maximum, the high voltage application durations are longer than necessary and can unnecessarily extend the arc and the steam bubble well beyond a time required to produce a shock wave of maximum intensity. The result is wasted energy, extended electrode erosion, and unnecessary heating of the adjoining tissue.

Hence, there is a need in the art to be able to control the energy applied to the electrodes of an electrical arc shock wave generator. More particularly, there is a need to control the applied energy to assure appropriate bubble and shock wave formation while at the same time conserving electrode material and assuring tissue safety. The present invention addresses these and other issues.

SUMMARY OF THE INVENTION

In one embodiment, a method for controlling the delivery of shock waves to treat calcified lesions in the wall of a blood vessel of a patient is disclosed. The method includes positioning an angioplasty catheter device within the blood vessel of the patient. The catheter device includes an angioplasty balloon surrounding an arc generator. The angioplasty catheter includes a central guide wire sheath for receiving a guide wire therein. The angioplasty balloon is inflated within the vessel with a conductive fluid. A plurality of voltage pulses from a power source are delivered to the arc generator disposed within the angioplasty balloon. The arc generator comprises a first electrode and a second electrode. During each pulse, signals representing values of a current flow between the first electrode and the second electrode are monitored by a current sensor. When the current reaches a predetermined value, a switch is switched to disconnect the power source from the arc generator and terminate that voltage pulse. The energy in each voltage pulse is sufficient to ensure creation of a respective plasma arc by the arc generator, creating a respective expansion shock wave conducted through the conductive fluid and through the angioplasty balloon to the vessel, thereby delivering energy to the calcified lesions within a wall of the vessel to break apart the lesions. The predetermined value is selected to compensate for the variable dwell time between initial application of each pulse and creation of the respective plasma arc in order to minimize excess energy delivered to the arc generator.

In another embodiment, a method of delivering shock waves to treat calcified lesions is disclosed. The method includes advancing an elongated carrier through a body lumen to reach the calcified lesion. The carrier includes a flexible member mounted near the distal end of the elongated carrier. A pair of electrodes are disposed within the flexible member. The flexible member is filled with a conductive fluid. A series of voltage pulses from a power source are delivered to the electrodes through a switch. Each voltage pulse has a voltage between 500 volts and 10,000 volts. Each pulse has sufficient energy to generate an arc in the fluid within the flexible member, allowing current to flow across the pair of electrodes to produce a shock wave associated with the expansion of a steam bubble. A dwell time between initial application of a given voltage pulse and creation of the arc is variable from pulse to pulse. During each voltage pulse, the current flowing across the pair of electrodes is monitored. When the sensed current reaches a predetermined value for a given pulse, that pulse is terminated using the switch. The predetermined value is selected to ensure the creation of the arc while compensating for the variable dwell time thereby minimizing excess energy delivered to the pair of electrodes.

In another embodiment, a method of delivering shock waves to treat calcified lesions in the wall of a blood vessel is disclosed. The method includes advancing an elongated angioplasty carrier through a blood vessel to reach the calcified lesion. The angioplasty carrier includes an angioplasty balloon mounted near the distal end of the angioplasty carrier. A pair of electrodes is disposed within the balloon. The balloon is filled with a conductive fluid. A series of voltage pulses from a power source are supplied to the electrodes through a switch, each voltage pulse having a voltage between 500 volts and 10,000 volts. Each voltage pulse has sufficient energy to generate an arc in the fluid within the balloon that allows current to flow across the pair of electrodes to produce a shock wave in the conductive fluid. A dwell time between initial application of a given voltage pulse and creation of the arc is variable from pulse to pulse. The current flowing across the pair of electrodes is monitored with a sensor during each voltage pulse. For each given voltage pulse, a delay period is initiated when the sensed current reaches a predetermined value. Once the delay period is over, the active voltage pulse is terminated by switching the switch. The predetermined value and the delay period are selected to ensure the creation of the arc while compensating for the variable dwell time thereby minimizing excess energy delivered to the pair of electrodes.

In another embodiment, a system includes a catheter including an elongated carrier and a balloon about the carrier in sealed relation thereto. The balloon is arranged to receive a fluid therein that inflates the balloon. The catheter further includes first and second electrodes within the balloon arranged to receive there-across a high electrical voltage at an initial low current. The high electrical voltage causes an electrical arc to form across the first and second electrodes within the balloon. The electrical arc creates a gas bubble within the liquid, a high current to flow through the first and second electrodes, and a mechanical shock wave within the balloon. The system further includes a power source that provides the first and second electrodes with the high electrical voltage at the initial current and that terminates the high electrical voltage in response to the high current flow through the first and second electrodes.

The power source includes a current sensor that senses current flowing through the first and second electrodes. The current sensor causes the power source to terminate the high electrical voltage when the current flowing through the first and second electrodes reaches a predetermined limit. The predetermined limit may be on the order of fifty amperes.

The system may further include a temperature sensor within the balloon that senses temperature of the fluid within the balloon. The power source may be further responsive to the temperature sensor.

The temperature sensor may cause the power source to decrease energy applied to the first and second electrodes responsive to the temperature of the fluid within the balloon increasing to control the temperature of the fluid. The temperature sensor may cause the power source to decrease energy applied to the first and second electrodes responsive to the temperature of the fluid within the balloon increasing to above two degrees Celsius above ambient temperature.

Each pulse of the serial electrical high voltage pulses has an amplitude. The temperature sensor may cause the power source to decrease the energy applied to the first and second electrodes by decreasing the amplitude of the serial electrical high voltage pulses. Alternatively, the temperature sensor may cause the power source to decrease the energy applied to the first and second electrodes by temporarily terminating the serial electrical high voltage pulses.

The serial electrical high voltage pulses have a pulse rate. The temperature sensor may cause the power source to decrease the energy applied to the first and second electrodes by decreasing the pulse rate of the serial electrical high voltage pulses.

The balloon may be a dilation balloon. The dilation balloon may be an angioplasty balloon. In some applications, such as lithotripsy, a balloon may not be required.

The system may further include a timer that times a delay time in response to the high current flow through the first and second electrodes and the power source may terminate the high electrical voltage after the delay time is timed. The power source may include a current sensor that senses current flowing through the first and second electrodes and the current sensor may cause the timer to time the delay time when the current flowing through the first and second electrodes reaches a predetermined limit. The predetermined limit may be on the order of fifty amperes.

In another embodiment, a system includes a catheter including an elongated carrier having a guide wire lumen and a balloon having an inner surface about the carrier in sealed relation thereto. The balloon forms a channel with the carrier. The channel is arranged to receive a fluid that inflates the balloon. The catheter further includes first and second electrodes within the balloon, between the carrier and the inner surface of the balloon, arranged to receive there-across a high electrical voltage at an initial low current to cause an electrical arc to form across the first and second electrodes within the balloon. The electrical arc creates a gas bubble within the liquid, a high current to flow through the first and second electrodes, and a mechanical shock wave within the balloon. The system further includes a power source that provides the first and second electrodes with the high electrical voltage at the initial current and that terminates the high electrical voltage in response to the high current flow through the first and second electrodes.

In a further embodiment, a system includes a catheter including an elongated carrier and a balloon about the carrier in sealed relation thereto. The balloon is arranged to receive a fluid therein that inflates the balloon. The catheter further includes first and second electrodes within the balloon arranged to receive there-across a high electrical voltage at an initial low current to cause an electrical arc to form across the first and second electrodes within the balloon. The electrical arc creates a steam bubble within the liquid, a high current to flow through the first and second electrodes, and a mechanical shock wave within the balloon. The steam bubble increases the temperature of the fluid. The system further includes a temperature sensor within the balloon that senses temperature of the fluid within the balloon and a power source that provides the first and second electrodes with the high electrical voltage at the initial current and that controls energy provided by the high electrical voltage in response to the sensed temperature of the fluid within the balloon.

The temperature sensor causes the power source to decrease energy applied to the first and second electrodes responsive to the temperature of the fluid within the balloon increasing to control the temperature of the fluid. The temperature sensor causes the power source to decrease energy applied to the first and second electrodes responsive to the temperature of the fluid within the balloon increasing to about two degrees Celsius above ambient temperature.

Each pulse of the serial electrical high voltage pulses has an amplitude. The temperature sensor may alternatively cause the power source to decrease the energy applied to the first and second electrodes by decreasing the amplitude of the serial electrical high voltage pulses. The temperature sensor may alternatively cause the power source to decrease the energy applied to the first and second electrodes by temporarily terminating the serial electrical high voltage pulses.

The serial electrical high voltage pulses have a pulse rate. The temperature sensor may alternatively cause the power source to decrease the energy applied to the first and second electrodes by decreasing the pulse rate of the serial electrical high voltage pulses.

The carrier of the catheter may have a guide wire lumen. The balloon has an inner surface that with the carrier, forms a channel arranged to receive the fluid that inflates the balloon. The first and second electrodes may be disposed between the carrier and the inner surface of the balloon.

According to a further embodiment, the invention provides a method that includes the steps of providing a catheter including an elongated carrier, a balloon about the carrier in sealed relation thereto, the balloon being arranged to receive a fluid therein that inflates the balloon, and first and second electrodes within the balloon. The method further includes introducing the fluid into the balloon to inflate the balloon, applying an electrical voltage across the first and second electrodes to form an electrical arc across the first and second electrodes, sensing current flow through the first and second electrodes, and varying the application of the electrical voltage across the first and second electrodes in response to sensed current flow through the first and second electrodes after the electrical arc is formed across the first and second electrodes.

The varying step may include terminating the application of the electrical voltage across the first and second electrodes. The high electrical voltage may be terminated when the current flowing through the first and second electrodes reaches a predetermined limit. The predetermined limit may be on the order of fifty amperes.

The method may include the further step of sensing temperature of the fluid within the balloon and the varying step may include varying the application of the electrical voltage across the first and second electrodes in response to sensed temperature of the fluid.

The varying step may include decreasing energy applied to the first and second electrodes responsive to the temperature of the fluid within the balloon increasing to control the temperature of the fluid. The energy applied to the first and second electrodes may be decreased responsive to the temperature of the fluid within the balloon increasing to above two degrees Celsius above ambient temperature.

The applying step may include applying energy in the form of serial electrical high voltage pulses and the varying step may further include decreasing the energy applied to the first and second electrodes by temporarily terminating the serial electrical high voltage pulses.

The serial electrical high voltage pulses have a pulse rate. Alternatively, the varying step may further include decreasing the energy applied to the first and second electrodes by decreasing the pulse rate of the serial electrical high voltage pulses.

The method may include the further step of timing a delay time in response to sensed current flow through the first and second electrodes and the varying step may include terminating the application of the electrical voltage across the first and second electrodes after timing the delay time. The delay time may be timed when the current flowing through the first and second electrodes reaches a predetermined limit. The predetermined limit may be on the order of fifty amperes.

According to another embodiment, a method includes the steps of providing a catheter including an elongated carrier, a balloon about the carrier in sealed relation thereto, the balloon being arranged to receive a fluid therein that inflates the balloon, and first and second electrodes within the balloon. The method further includes the steps of introducing the fluid into the balloon to inflate the balloon, applying energy in the form of an electrical voltage across the first and second electrodes to form an electrical arc across the first and second electrodes, sensing temperature of the fluid within the balloon, and varying the application of the energy across the first and second electrodes in response to sensed temperature of the fluid within the balloon.

The varying step may include decreasing the energy applied to the first and second electrodes responsive to the temperature of the fluid within the balloon increasing. The varying step may include decreasing the energy applied to the first and second electrodes responsive to the temperature of the fluid within the balloon increasing to about two degrees Celsius above ambient temperature.

Each pulse of the serial electrical high voltage pulses has an amplitude. The varying step may include decreasing the energy applied to the first and second electrodes by decreasing the amplitude of the serial electrical high voltage pulses.

The applying step may include applying energy in the form of serial electrical high voltage pulses and the varying step may further include decreasing the energy applied to the first and second electrodes by temporarily terminating the serial electrical high voltage pulses.

The applying step may include applying energy in the form of serial electrical high voltage pulses, wherein the serial electrical high voltage pulses have a pulse rate. The varying step may further include decreasing the energy applied to the first and second electrodes by decreasing the pulse rate of the serial electrical high voltage pulses.

In a still further embodiment, a system treats obstructions within bodily fluid and includes a catheter including first and second electrodes arranged to receive there-across a high electrical voltage at an initial low current. The high electrical voltage causes an electrical arc to form across the first and second electrodes. The electrical arc creates a gas bubble within the bodily fluid, a high current to flow through the first and second electrodes, and a mechanical shock wave within the bodily fluid. The system further includes a power source that provides the first and second electrodes with the high electrical voltage at the initial current and that terminates the high electrical voltage in response to the high current flow through the first and second electrodes.

The energy applied by the power source may be in the form of serial electrical high voltage pulses. Each pulse of the serial electrical high voltage pulses has an amplitude. The power source may control the energy applied to the first and second electrodes by varying the amplitude of the serial electrical high voltage pulses.

The serial electrical high voltage pulses have a pulse rate. Alternatively, the power source may vary the energy applied to the first and second electrodes by varying the pulse rate of the serial electrical high voltage pulses.

The system may further include a timer that times a delay time in response to the high current flow through the first and second electrodes and the power source may terminate the high electrical voltage after the delay time is timed. The power source may include a current sensor that senses current flowing through the first and second electrodes and the current sensor may cause the timer to time the delay time when the current flowing through the first and second electrodes reaches a predetermined limit. The predetermined limit may be on the order of fifty amperes.

In still a further embodiment, a method includes the steps of providing a catheter including first and second electrodes, applying an electrical voltage across the first and second electrodes to form an electrical arc across the first and second electrodes, sensing current flow through the first and second electrodes, and varying the application of the electrical voltage across the first and second electrodes in response to sensed current flow through the first and second electrodes after the electrical arc is formed across the first and second electrodes.

The applying step may include applying energy in the form of serial electrical high voltage pulses, the serial electrical high voltage pulses having a pulse rate, and wherein the varying step further includes controlling the energy applied to the first and second electrodes by varying the pulse rate of the serial electrical high voltage pulses.

The serial high voltage pulses have amplitudes. The varying step may alternatively or in addition include controlling the energy applied to the first and second electrodes by varying the amplitude of the serial electrical high voltage pulses.

The method may include the further step of timing a delay time in response to sensed current flow through the first and second electrodes and the varying step may include terminating the application of the electrical voltage across the first and second electrodes after timing the delay time. The delay time may be timed when the current flowing through the first and second electrodes reaches a predetermined limit. The predetermined limit may be on the order of fifty amperes.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
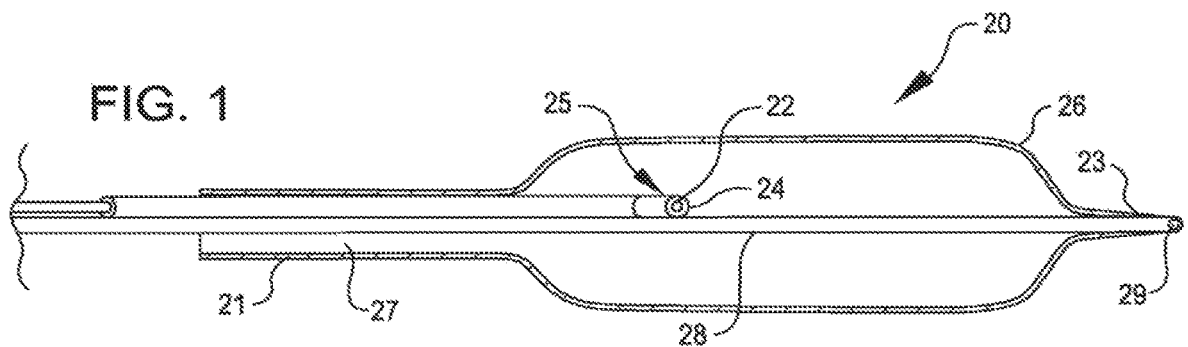
FIG. 1 is a simplified side view of an angioplasty balloon catheter of the type that may utilize various embodiments of the invention to advantage.

FIG. 1 is a simplified side view of an angioplasty balloon catheter 20 of the type that may utilize various embodiments of the invention to advantage. The catheter 20 includes an elongated carrier, such as a hollow sheath 21, a dilating balloon 26 formed about the sheath 21 in sealed relation thereto and a guide wire member 28 to which the balloon is sealed at a seal 23. The guide wire member has a longitudinal lumen 29 through which a guide wire (not shown) may be received for directing the catheter 20 to a desired location within a vein or artery, for example.

The sheath 21 forms with the guide wire member 28 a channel 27 through which fluid, such as saline, may be admitted into the balloon to inflate the balloon. The channel 27 further permits the balloon 26 to be provided with an electrode pair 25 including electrodes 22 and 24 within the fluid filled balloon 26.

Figure 2:
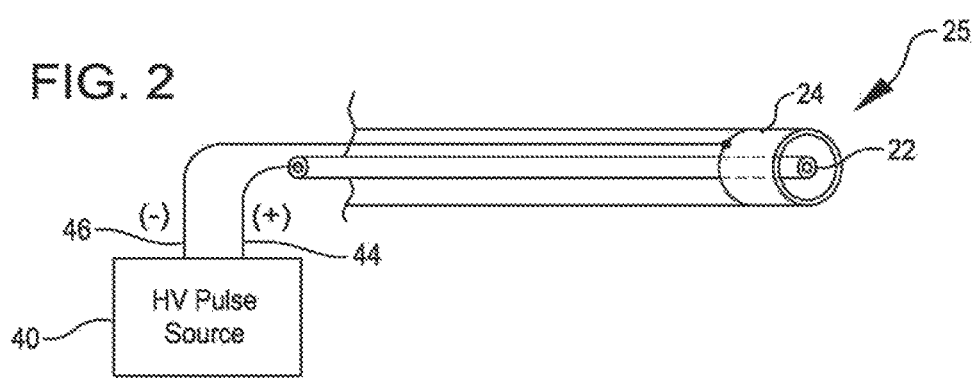
FIG. 2 is a simplified side view of an electrode structure that may be employed in the catheter of FIG. 1 coupled to a source of high voltage pulses according to one embodiment of the invention.
Figure 3:
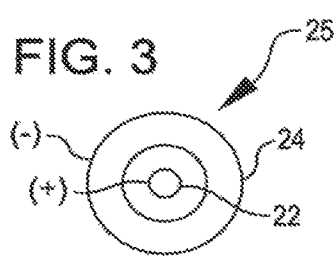
FIG. 3 is a front plan view of the electrode structure of FIG. 2.

As may be seen in FIG. 2, the electrodes 22 and 24 are attached to a source 40 of high voltage pulses. As may be seen in FIG. 3, the electrodes 22 and 24 are coaxially disposed with electrode 22 being a center electrode and electrode 24 being a ring shaped electrode about electrode 22. The center electrode 22 is coupled to a positive terminal 44 of source 40 and the ring electrode 24 is coupled to a negative terminal 46 of the source 40. The electrodes 22 and 24 are formed of metal, such as stainless steel, and are maintained a controlled distance apart to allow a reproducible arc to form for a given applied voltage and current.

The electrical arcs between electrodes 22 and 24 in the fluid are used to generate shock waves in the fluid. Each pulse of high voltage applied to the electrodes 22 and 24 forms an arc across the electrodes. The voltage pulses may have amplitudes as low as 500 volts, but preferably, the voltage amplitudes are in the range of 1000 volts to 10,000 volts The balloon 26 may be filled with water or saline in order to gently fix the balloon in the walls of the artery or vein, for example, in direct proximity with the calcified lesion. The fluid may also contain an x-ray contrast to permit fluoroscopic viewing of the catheter during use. Once the catheter 20 is positioned with the guide wire (not shown), the physician or operator can start applying the high voltage pulses to the electrodes to form the shock waves that crack the calcified plaque. Such shockwaves will be conducted through the fluid, through the balloon, through the blood and vessel wall to the calcified lesion where the energy will break the hardened plaque without the application of excessive pressure by the balloon on the walls of the artery.

Figure 4:
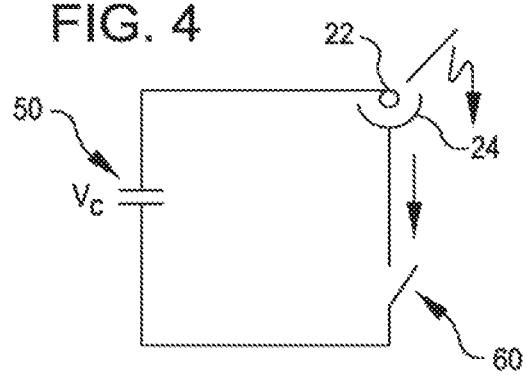
FIG. 4 is a simplified equivalent circuit diagram of a system according to an embodiment of the invention.

FIG. 4 is a simplified equivalent circuit diagram of a system according to an embodiment of the invention. Here it may be seen that a capacitance stores a high voltage. When a switch 60 is closed, the voltage drop across the electrodes 22 and 24 begins to quickly rise at an initially low current level. After a dwell time, when the voltage across the electrodes reaches the breakdown voltage of the fluid between the electrodes, an electrical arc occurs across the electrodes. The arc causes a steam bubble to form between the electrodes and a relatively high current to flow through the electrodes. The expansion of the bubble forms a first or leading edge shock wave. After a time, the steam bubble cools and condenses causing the bubble to collapse. The collapsing bubble has the potential for forming a second or trailing edge shock wave. As previously mentioned, the trailing edge shock wave is relatively unreliable exhibiting inconsistent intensities from shock wave to shock wave. Hence, it is the leading edge shock wave that holds the most promise for reliable therapy.

It has been found that effective shock wave intensity may be accomplished without holding the high voltage pulses on during the entire extent of their corresponding steam bubbles. Moreover, terminating the application of the high voltage before steam bubble collapse can serve to preserve electrode material, permitting a pair of electrodes to last for an increased number of applied high voltage pulses. Still further, as will be seen subsequently, early termination of the high voltage can also be used to advantage in controlling the temperature within the balloon fluid.

Figure 5:
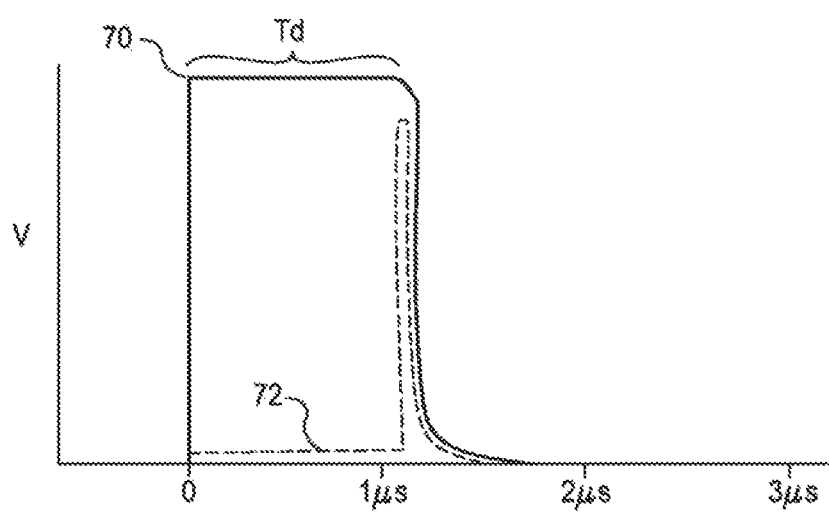
FIG. 5 is a graph illustrating a high voltage pulse applied to a pair of electrical arc shock wave producing electrodes and the resulting current flow through the electrodes in accordance with an embodiment of the invention.

FIG. 5 is a graph illustrating a high voltage pulse applied to a pair of electrical arc shock wave producing electrodes and the resulting current flow through the electrodes in accordance with an embodiment of the invention. When the switch 60 (FIG. 4) is first closed, the voltage across the electrodes quickly rises to a level 70. During this time, as shown by dashed lines 72, the current through the electrodes is relatively low. After a dwell time (Td), the arc occurs between the electrodes. At this time the steam bubble begins to form and a high current begins to flow through the electrodes. In accordance with embodiments of the invention, responsive to the current through the electrodes, the application of the high voltage is terminated. This conserves energy applied to the electrodes, causing the electrodes to remain useful for a greater number of pulses than otherwise would be the case if the high voltage were applied longer or sustained throughout the bubble existence. The advantages of controlling the applied energy in this manner are obtained without adversely affecting the intensity of the leading edge shock waves produced.

Figure 6:
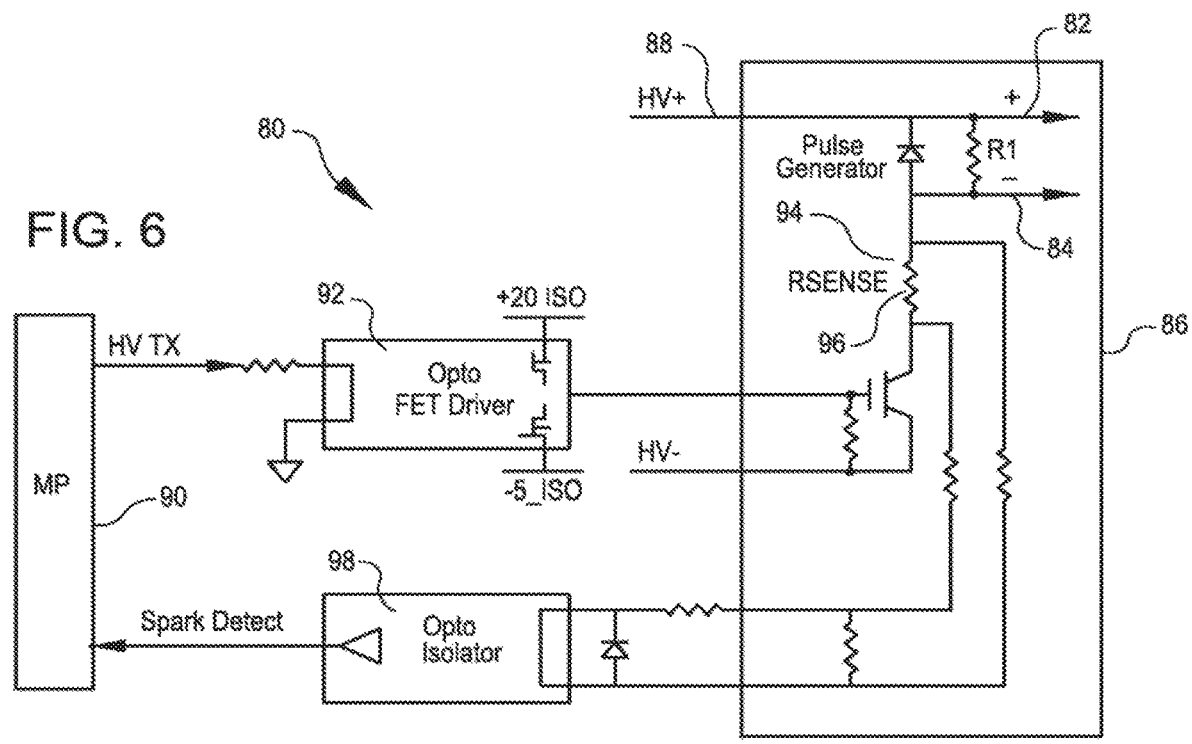
FIG. 6 is a schematic diagram of a power source for use in an angioplasty electrical arc shock wave angioplasty catheter according to an embodiment of the invention.

FIG. 6 is a schematic diagram of a power source 80 for use in an electrical arc shock wave angioplasty catheter according to an embodiment of the invention. The power source 80 has an output terminal 82 that may be coupled to electrode 22 of FIG. 1 and an output terminal 84 that may be coupled to electrode 24 of FIG. 1. A switch circuit 86 selectively applies a high voltage on line 88 across the electrodes. A microprocessor 90, or other similar control circuitry, such as a gate array, controls the overall operation of the source 80. A Field Programmable Gate Array (FPGA) may also be substituted for the microprocessor in a manner know in the art. The microprocessor 90 is coupled to the switch 86 by an optical driver 92. The switch includes a current sensor 94 that includes a current sensing resistor 96 that generates a signal that is applied to an optical isolator 98 when the current flowing through the electrodes reaches a predetermined limit, such as, for example, fifty (50) amperes.

In operation, the microprocessor 90 through the optical driver 92, causes the switch 86 to apply the high voltage to the electrodes 22 and 24. The current sensed through resister 96 is monitored by the microprocessor 90 through the optical isolator 98. When the current flowing through the electrodes reaches a predetermined limit, as for example 50 amperes, the microprocessor 90 causes the application of the high voltage to be terminated. The forgoing occurs for each high voltage pulse applied to the electrodes 22 and 24. Each pulse creates a shock wave of consistent and useful intensity. Further, because the application of the high voltage is terminated early, the electrode material is preserved to lengthen the useful life of the electrodes.

Figure 7:
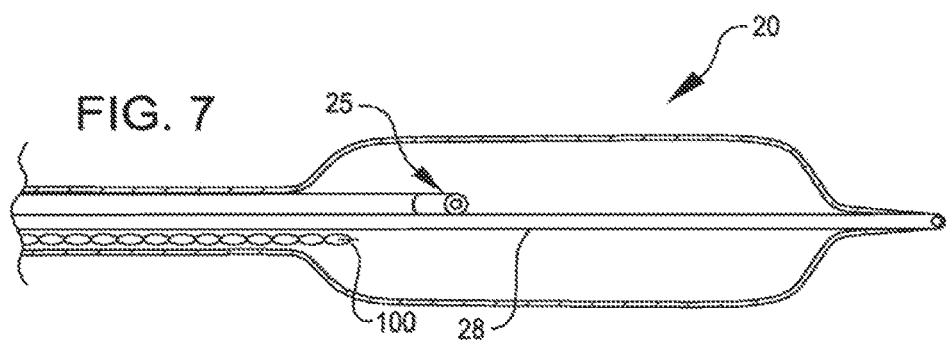
FIG. 7 is a side view of a dilating catheter with an electrical arc producing electrode structure and a temperature probe therein according to aspects of the invention.

FIG. 7 is a side view of a dilating catheter with an electrical arc producing electrode structure and a temperature probe therein according to aspects of the invention. The catheter 20 of FIG. 7 may be the same catheter as shown in FIG. 1. Here however, the catheter 20 further includes a temperature probe or sensor 100. The temperature sensor may be employed for sensing the temperature of the fluid within the balloon. Preferably, the temperature of the fluid within the balloon 26 should not be permitted to rise more than two degrees Celsius above the ambient body temperature. If this were to occur, soft tissue damage may result.

Figure 8:
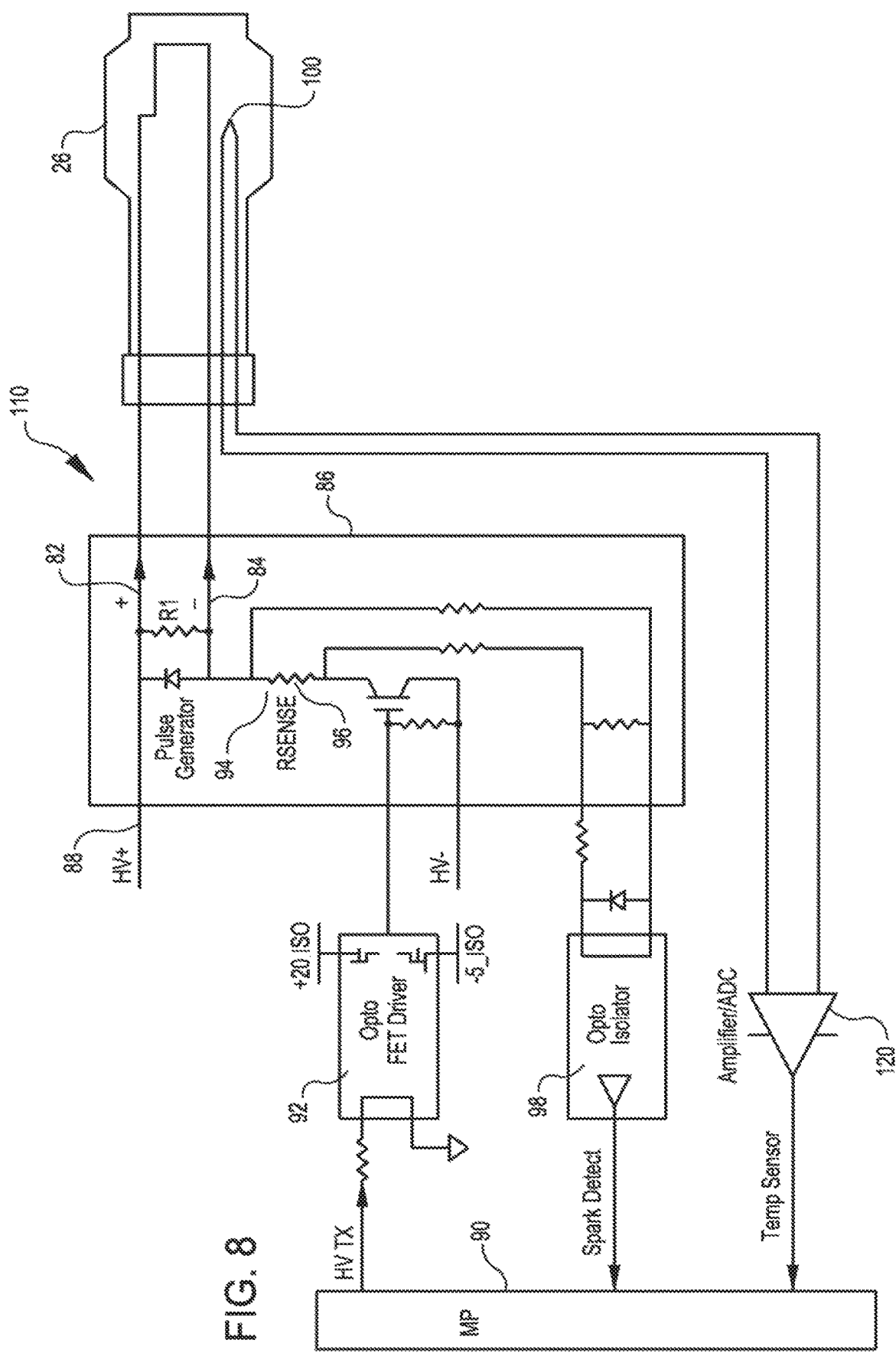
FIG. 8 is a schematic diagram of an angioplasty catheter system according to further embodiments of the invention.

FIG. 8 is a schematic diagram of an angioplasty catheter system 110 according to further embodiments of the invention which includes the catheter 20 and temperature probe 100. Here the system also includes the microprocessor 90, the switch 86, optical driver 92 and optical isolator 98. All of these elements may function as previously described. In addition, the temperature sensor 100 conveys a temperature signal through another optical isolator 120 indicative of the temperature of the fluid within the balloon 26. If the temperature within the balloon 26 rises to more than a certain temperature, for example to more than two degrees Celsius above ambient body temperature, the energy applied to the electrodes is decreased. This will decrease the size and duration of the steam bubbles produced by the electrodes to maintain the temperature of the fluid within the balloon to within safe limits. The microprocessor 90 may cause the switch 86 to decrease the pulse amplitude of the applied high voltage pulses or the pulse rate of the applied high voltage pulse. It could alternatively temporarily terminate the application of the pulses.

Figure 9:
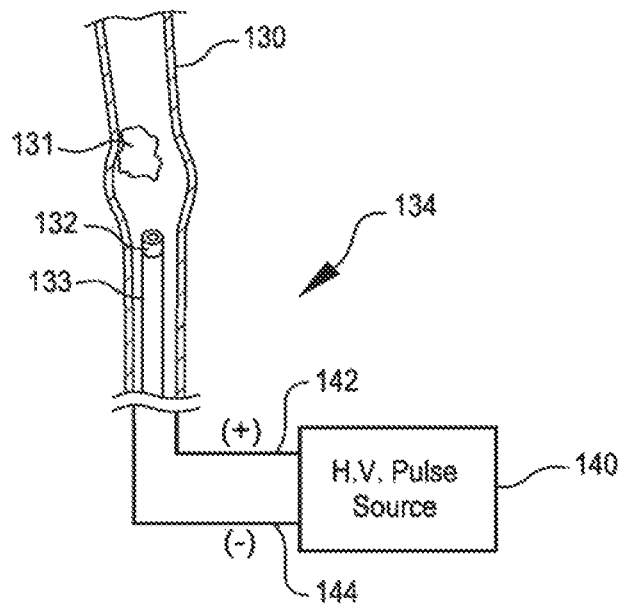
FIG. 9 is a simplified side view, partly in section, of a further embodiment wherein a balloon is not required.

FIG. 9 is a simplified side view, partly in section, of a further embodiment wherein a balloon is not required. In this embodiment, a system 134, according to further aspects of the invention, is shown treating an obstruction, more particularly, a kidney stone 131. The system includes a catheter 133 that terminates at its distal end with an electrode pair 132 similar to electrode pair 25 of FIGS. 1 and 2. The system further includes a power source 140. The power source has a positive output terminal 142 and a negative output terminal 144. The center electrode of the electrode pair 132 may be coupled to the positive terminal 142 of source 140 and the ring electrode of the electrode pair 132 may be coupled to the negative terminal 144 of the source 140. The electrodes of the electrode pair 132 may be formed of metal, such as stainless steel, and are maintained a controlled distance apart to allow a reproducible arc to form for a given applied voltage and current.

The catheter 133 of system 134 is shown in a ureter 130. The ureter has a kidney stone 131 requiring treatment. According to this embodiment, voltage pulses are applied to the electrode pair 132 to produce leading edge shock waves as previously described. The shock waves propagate through the fluid within the ureter and impinge directly on the kidney stone 131. In a manner as previously described, the power source may be operated to maintain the energy applied to the electrode pair within limits to assure that the steam bubbles produced by the generated arcs do not harm the ureter. To that end, the amplitude or pulse rate of the applied voltages may be controlled. Hence, by controlling the energy of the current during the produced arc, such as by controlling the on time of the current, barotrauma to the ureter may be minimized even though a balloon is not employed as in previous embodiments. Of course, the system of FIG. 9 may be used in other body organs as well, such as the bile duct, for example.

Figure 10:
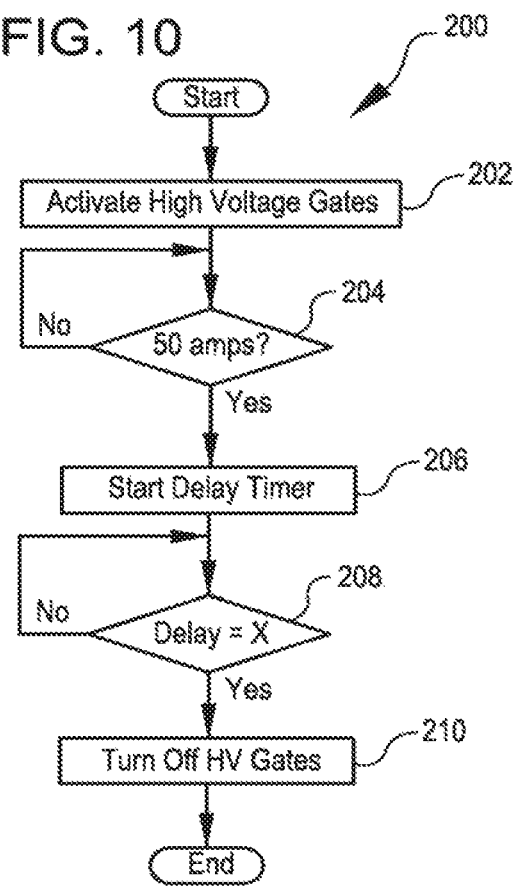
FIG. 10 is a flow diagram illustrating a further embodiment of the invention.

FIG. 10 is a flow diagram illustrating the process of a further embodiment of the invention. The embodiment of FIG. 10 takes into account the time it takes for a high voltage switch, such as switch 86 (FIG. 6), to turn off (the turn off time) and the rise time of the current flowing through the electrodes once the electrical arc starts. The current through the electrodes can eventually reach one-hundred amperes or more, at which point the maximum intensity shock wave will be formed. In order to permit the maximum current to be reached and to account for the turn off time of the switch 86, a delay is timed extending from when the current flowing through the electrodes is at a fixed threshold known to be below the maximum current, to the turn off time of the switch before the expected current maximum. For example, the current threshold may be fifty amperes. When the current through the electrodes equals fifty amperes, the delay timing is begun by the starting of a delay timer within the microprocessor 90. If the current is expected to be at a maximum 200 nanoseconds after the current reaches fifty amperes, and if it takes 100 nanoseconds for the high voltage switch to actually turn off after receiving a turn off signal, a delay of 100 nanoseconds should be timed from the 50 ampere sensing before a turn off signal is applied to the high voltage switch. Hence, a total time of 200 nanoseconds will pass after the current reaches 50 amperes and, as a result, will reach its maximum. As the current reaches its maximum, or shortly thereafter, the voltage applied to the electrodes will be terminated.

Referring now to the flow diagram 200 of FIG. 10, and also with reference to FIG. 6, the process begins with activity step 202 wherein the high voltage is applied to the output terminals 82 and 84 for application to the electrodes, for example, electrodes 22 and 24 (FIG. 1). At first, the current initially flowing through the electrodes is relatively low. However, after a dwell time, the applied high voltage causes an electrical arc to begin to form between the electrodes, the current through the electrodes is sensed, and the current rapidly rises. The current through the electrodes is sensed as previously described. At decision block 204, the microprocessor 90 determines if the sensed current has reached fifty amperes. When the current reaches fifty amperes, the process advances to activity block 206 where the timing of the aforementioned delay time (x) is started. Next, in decision block 208, it is determined when the delay time has been timed. In accordance with this embodiment, the delay time (x) may be 100 nanoseconds. When the delay time of 100 nanoseconds is timed, the process advances to activity block 210 wherein the process completes with a turn off signal being applied by the microprocessor 90 to the high voltage switch 86. The switch 86 will actually turn of a turn of time after the turn off signal is applied to the switch 86. Since it takes 100 nanoseconds for the switch to turn off and since 100 nanoseconds are timed before the turn off signal is applied to the switch, 200 nanoseconds form the 50 ampere current sensing will pass before the applied voltage to the electrodes is actually terminated. That provides sufficient time for the current to reach its maximum to generate the maximum intensity shock wave. The voltage application will terminated as the current reaches maximum, or shortly thereafter.

As a result of the foregoing, a maximum intensity shock wave is formed without wasting energy, without unduly eroding the electrodes, and without generating unnecessary heat. As may be appreciated, the delay timing may be employed to advantage in each of the embodiments disclosed herein including the embodiment of FIG. 9 which does not require a balloon.

The subject method can be used with various electrode designs. For example, the electrodes can be provided with a low profile to improve the ability of the catheter to navigate small vessels. An example of such a low profile electrode design can be found in U.S. Pat. No. 8,747,416. It may also desirable to alternate the polarity of the voltage pulses to even up the wear on the electrodes. An example of an approach for alternating the polarity of the voltage pulses can be found in U.S. Pat. No. 10,226,265.

While particular embodiments of the present invention have been shown and described, modifications may be made. It is therefore intended in the appended claims to cover all such changes and modifications which fall within the true spirit and scope of the invention as defined by those claims.

What is claimed is:

1. A method for controlling delivery of shock waves to treat calcified lesions in the wall of a blood vessel of a patient, the method comprising:

positioning an angioplasty catheter device within the blood vessel of the patient, the catheter device comprising an angioplasty balloon surrounding an arc generator, the angioplasty catheter including a central guide wire sheath for receiving a guide wire therein;

inflating the angioplasty balloon of the catheter device within the vessel with a conductive liquid; and delivering, via a power source, a plurality of voltage pulses to the arc generator disposed within the angioplasty balloon, wherein the arc generator comprises a first electrode and a second electrode, and delivering the plurality of voltage pulses comprises, for each pulse of the plurality of voltage pulses, applying a voltage to the arc generator, monitoring signals representing values of a current flow between the first electrode and the second electrode caused by the voltage, wherein the signals are generated by a current sensor, and terminating the voltage to the arc generator to complete the respective pulse, wherein terminating comprises i) receiving a respective signal from the current sensor indicative of a current of at least a predetermined value, and ii) causing switching of a switch to disconnect the power source from the arc generator;

wherein each pulse of the plurality of voltage pulses is sufficient to ensure creation of a respective plasma arc by the arc generator, creating a respective expansion shock wave conducted through the conductive liquid and through the angioplasty balloon to the vessel, thereby delivering energy to the calcified lesions within the wall of the vessel to break apart the lesions, wherein a respective dwell time between initial application of each pulse and creation of the respective plasma arc varies from pulse to pulse, and the predetermined value is selected to compensate for the variable dwell times and minimize excess energy delivered to the arc generator.

2. The method of claim 1, wherein the switch is a solid state switch.

3. The method of claim 1, further comprising adding a contrast medium to the conductive liquid for imaging the catheter device during treatment.

4. The method of claim 1, wherein:

applying the voltage to the arc generator comprises applying the voltage via output terminals of the power source; and monitoring the signals representing the values of the current flow comprises monitoring a voltage drop across a resistor connected to one of the output terminals.

5. The method of claim 1, wherein terminating the voltage to the arc generator comprises beginning a delay timer responsive to receiving the respective signal, and terminating the voltage upon completion of a predetermined period according to the delay timer.

6. The method of claim 1, wherein the voltage of each pulse of the plurality of voltage pulses is between 500 volts and 10,000 volts.

7. The method of claim 1, wherein the voltage of each pulse of the plurality of voltage pulses is between 1000 volts and 10,000 volts.

8. The method of claim 1, wherein the predetermined current value is selected to ensure the creation of the expansion shock wave associated with the expansion of a steam bubble and minimize energy available for a trailing shock wave associated with the subsequent collapse of the steam bubble.

9. A method of delivering shock waves to treat calcified lesions comprising:

advancing an elongated carrier through a body lumen to reach the calcified lesion, said carrier having a flexible member mounted near the distal end of the elongated carrier, said flexible member having a pair of electrodes disposed therein;

filling the flexible member with a conductive liquid;

delivering a series of voltage pulses from a power source to the electrodes through a switch, each voltage pulse having a voltage between 500 volts and 10,000 volts, each voltage pulse having sufficient energy to generate an arc in the liquid within the flexible member and allowing current to flow across the pair of electrodes to produce a shock wave associated with the expansion of a steam bubble, wherein a dwell time between initial application of a given voltage pulse and creation of the arc is variable from pulse to pulse;

sensing the current flowing across the pair of electrodes during each voltage pulse; and for each given voltage pulse, initiating the termination of the given voltage pulse when the sensed current reaches a predetermined value, wherein the termination includes switching the switch, the predetermined value being high enough to ensure the creation of the arc while compensating for the variable dwell time thereby minimizing excess energy delivered to the pair of electrodes.

10. The method of claim 9, wherein the initiating the termination of the given voltage pulse includes activating a delay timer in response to the sensing of the current reaching the predetermined value prior to the switch being switched.

11. The method of claim 9, wherein the switch is a solid state switch.

12. The method of claim 9, further comprising adding a contrast medium to the conductive liquid for imaging the carrier during treatment.

13. The method of claim 9, wherein sensing the current comprises sensing the current using a current sensor including a resistor and wherein the voltage drop across the resistor is monitored to determine the current flowing between the pair of electrodes.

14. The method of claim 9, wherein the voltage of each pulse of the plurality of voltage pulses is between 1000 volts and 10,000 volts.

15. The method of claim 9, wherein the predetermined value is selected to ensure the creation of the shock wave associated with the expansion of a steam bubble and minimize energy available for a trailing shock wave associated with the subsequent collapse of the steam bubble.

16. A method of delivering shock waves to treat calcified lesions in the wall of a blood vessel comprising:

advancing an elongated angioplasty carrier through a blood vessel to reach the calcified lesion, said angioplasty carrier having an angioplasty balloon mounted near the distal end of the angioplasty carrier, said balloon having a pair of electrodes disposed therein;

filling the balloon with a conductive liquid;

delivering a series of voltage pulses from a power source to the electrodes through a switch, each voltage pulse having a voltage between 500 volts and 10,000 volts, each voltage pulse having sufficient energy to generate an arc in the liquid within the balloon and allowing current to flow across the pair of electrodes to produce a shock wave in the conductive liquid, wherein a dwell time between initial application of a given voltage pulse and creation of the arc is variable from pulse to pulse;

monitoring a current sensor to sense the current flowing across the pair of electrodes during each voltage pulse; and for each given voltage pulse, initiating a delay period when the sensed current reaches a predetermined value, once the delay period is over, initiating the termination of the given voltage pulse, wherein the termination includes switching the switch, and wherein the predetermined value and the delay period are selected to ensure the creation of the arc while compensating for the variable dwell time thereby minimizing excess energy delivered to the pair of electrodes.

17. The method of claim 16, wherein the switch is a solid state switch.

18. The method of claim 16, further comprising adding a contrast medium to the conductive liquid for imaging the carrier during treatment.

19. The method of claim 16 wherein the current sensor includes a resistor and wherein the voltage drop across the resistor is monitored to determine the current flowing between the pair of electrodes.

20. The method of claim 16, wherein the predetermined current value and the delay period are selected to ensure the creation of an expansion edge shock wave associated with the expansion of a steam bubble and minimize energy available for a trailing shock wave associated with the subsequent collapse of the steam bubble.

* * * * *